United States Patent [19]

Aizawa et al.

[11] Patent Number: 5,567,409
[45] Date of Patent: Oct. 22, 1996

[54] METHOD AND MEDICAL AGENT FOR DIAGNOSIS OF ARTHRITIS

[75] Inventors: Katsuo Aizawa, Yokohama; Yukari Kuroiwa, Urawa, both of Japan

[73] Assignee: Nippon Petrochemicals Company, Ltd., Tokyo, Japan

[21] Appl. No.: 353,882

[22] Filed: Dec. 12, 1994

Related U.S. Application Data

[62] Division of Ser. No. 229,940, Apr. 19, 1994, Pat. No. 5,430,051.

[30] Foreign Application Priority Data

Apr. 22, 1993 [JP] Japan ................... 5-120977

[51] Int. Cl.$^6$ ................ A61K 49/00; A61K 31/40
[52] U.S. Cl. ................ 424/9.363; 424/9.3; 424/9.364; 514/410; 514/825
[58] Field of Search ................ 514/410, 825; 424/9.3, 9.363, 9.364

[56] References Cited

U.S. PATENT DOCUMENTS

| | | | |
|---|---|---|---|
| 4,649,151 | 3/1987 | Dougherty et al. | 514/410 |
| 4,656,186 | 4/1987 | Bommer et al. | 514/410 |
| 4,675,338 | 6/1987 | Bommer et al. | 514/410 |
| 4,693,885 | 9/1987 | Bommer et al. | 424/2 |
| 4,977,177 | 12/1990 | Bommer et al. | 514/410 |
| 4,997,639 | 3/1991 | Aizawa et al. | 424/9 |
| 5,004,811 | 4/1991 | Bommer et al. | 540/145 |
| 5,028,594 | 7/1991 | Carson | 514/23 |
| 5,066,274 | 11/1991 | Bommer et al. | 604/20 |
| 5,308,861 | 5/1994 | Aizawa et al. | 514/410 |
| 5,368,841 | 11/1994 | Trauner et al. | 424/9 |

*Primary Examiner*—Theodore J. Criares
*Attorney, Agent, or Firm*—Scully, Scott, Murphy & Presser

[57] ABSTRACT

A method and medical agents for the photodynamic diagnosis of rheumatoid arthritis of mammals, which agent comprises at least one member of fluorescent compounds selected from the group consisting of tetrapyrrole carboxylic acids having at least one carboxyl group, corresponding di- or tetrahydrotetrapyrrole carboxylic acids, and mono-, di- or polyamides of the tetrapyrrole carboxylic acids with amino-mono- or dicarboxylic acids and their salts.

9 Claims, No Drawings

METHOD AND MEDICAL AGENT FOR DIAGNOSIS OF ARTHRITIS

This is a divisional of application Ser. No. 08/229,940, filed on Apr. 19, 1994, now U.S. Pat. No. 5,430,051.

BACKGROUND OF THE INVENTION

(1) Field of the Invention

This invention relates to a method and medical agents for the photodynamic diagnosis and photodynamic therapy of the arthritis, especially the arthritis of mammals. More particularly, the medical agents used in the present invention belong to specific fluorescent compounds having a tetrapyrrole skeletal structure. When an effective quantity of the medical agent is administered to an animal patient, the agent is accumulated in the affected part of the body.

When light rays of necessary wavelength are applied to an affected joint to be diagnosed or treated, the agent generates fluorescence in the affected portion, thereby enabling the detection of arthritis. This is called as photodynamic diagnosis. In the therapeutic treatment, when light rays of appropriate wavelength and intensity are applied to a lesion, the agent is excited to produce a cytotoxic effect and the affected cells in arthritic lesion are necrosed. This is called as photodynamic therapy. The present invention relates to the diagnosis and the therapy of this kind applied to arthritis, especially rheumatoid arthritis.

(2) Description of the Prior Art

Rheumatoid arthritis is a chronic systemic disease mainly causing to occur polyarthritis as a cardinal symptom. This disease is initiated by the pain and swelling in small joints of hands and feet, or in elbow joints and knee joints, and other joints in whole body are then affected little by little. In the initial phase of the disease, the hyperplasia of the synovia of the affected joint begins by some stimulation of the unknown antigen, and the synovial hyperplasia is maintained and prolonged by the monokine cascade system to be a tumor-like condition. The constituents of the joint such as cartilage or ligament or bone are destroyed by the enzymes produced by these synovia and followed by the destruction of the joints.

This pathological condition is observed in all human races and distributed all over the world.

In the diagnosis of the rheumatoid arthritis, it is necessary to identify the outbreak of rheumatoid factor and the existence of inflammatory response by means of blood test, the occurrence of swelling and pain in joints, and further the existence of distortion of bones by means of X-ray inspection. In view of the results of these inspections, the diagnosis of rheumatoid arthritis can be attained.

Since any satisfactory etiologic therapy for the rheumatoid arthritis has not been developed, the nosotropic treatment to preserve affected lesions is employed according to respective cases. However, the efficacy of such treatments is no yet clarified at present. That is, in the first place, medication is done in order to promote the remission of disease by administering a non-steroidal antiphlogistic lenitive, at the same time, the physiotherapy is adopted. In spite of the medication, if the swelling takes a bad turn and the hyperplasia of synovial membrane become noticeable, synovectomy is carried out by arthrotomy or by arthroscopic method. The total arthroplasty is employed in order to restore the function of the joint by substituting the artificial prosthesis for the destructed joint.

In order to prevent the destruction of the joint constituents, the cellular immunologic responses in the synovia must be reduced throughout the disease process, especially in the early stage.

There is hitherto known a method of diagnosis and therapy of rheumatoid arthritis by administering a hematoporphyrin derivative to rats which suffer from adjuvant induced arthritis and applying light rays to the rats. For instance, "Rheumatoid Arthritis and Laser (Effect of laser irradiation to adjuvant induced arthritis)", The RYUMACHI (Official Journal of the Japan Rheumatism Association), Vol. 23, pp 574–575, 1983.

However, it was clarified through the experiments carried out by the present inventors that, when a typical hematoporphyrin derivative, Photofrin II, is used, it cannot be taken selectively into a rheumatoid arthritic lesion and a noticeable therapeutic effect to the rheumatoid arthritis cannot be expected.

Incidentally, the compounds themselves used in the present invention are already known as diagnostic and therapeutic medicines for cancer. However, the inventors have never known any instance concerning the use of the relevant compounds for the diagnosis and treatment of arthritis. The field of art according to the present invention is, of course, different from the field of art in the diagnosis and the therapy of cancer.

Furthermore, the inventors are acquainted with the following literatures, however, the object of the studies are different from that of the present invention.

(a) "Systemic Immunosuppression Induced by Photodynamic Therapy (PDT) is Adoptively Transferred by Macrophages", PHOTOCHEMISTRY AND PHOTOBIOLOGY, Vol. 49, pp 453–458, 1989.

(b) "Immunological Suppression in Mice Treated with Hematoporphyrin Derivative Photoradiation", CANCER RESEARCH, Vol. 46, pp 1608–1611, 1986.

BRIEF SUMMARY OF THE INVENTION

It is, therefore, the object of the present invention to provide a medical agent for use in the diagnosis and the therapy of the above-mentioned rheumatoid arthritis. The present invention further propose a medical agent for the photodynamic diagnosis and photodynamic therapy of arthritis, especially rheumatoid arthritis, in which the conventional diagnostic method to use arthroscopes and synovectomy are sometimes employed.

In view of the above object, the present inventors have carried out extensive investigations and, as a result, they have found out a novel utility of medical agents, which agents are effective to the photodynamic diagnosis and photodynamic therapy of rheumatoid arthritis.

The present invention, therefore, provides a medical agents for use in the diagnosis and therapy of rheumatoid arthritis of mammals. The agents comprise at least one member of fluorescent compounds selected from the group consisting of tetrapyrrole carboxylic acids having at least one carboxyl group represented by the following general formula, corresponding di- or tetrahydrotetrapyrrole carboxylic acids, and mono-, di- or polyamides of said tetrapyrrole carboxylic acids with amino-monocarboxylic acid or amino-dicarboxylic acids, and their salts.

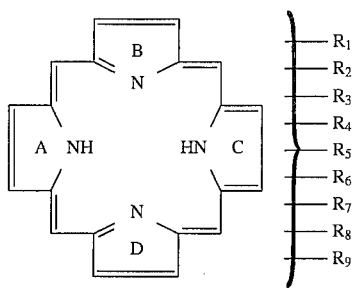

In the formula, $R_1$ is methyl, $$\begin{bmatrix} -H \\ -CH_3 \end{bmatrix} \text{or} \begin{bmatrix} -OH \\ -CH_3 \end{bmatrix};$$

$R_2$ is H, vinyl, ethyl, —CH(OH)CH$_3$, acetyl, $$\begin{bmatrix} -H & , -C=O, \\ -ethyl & | \\ & H \end{bmatrix}$$

—CH$_2$CH$_2$COOH or =CHCHO;
$R_3$ is methyl, $$\begin{bmatrix} -H \\ -CH_3 \end{bmatrix} \text{or} \begin{bmatrix} -CH_3; \\ -OH \end{bmatrix}$$

$R_4$ is H, vinyl, ethyl, —CH(OH)CH$_3$, —CH$_2$CH$_2$COOH, =CHCHO or $$\begin{bmatrix} -H \\ -ethyl \end{bmatrix};$$

$R_5$ is methyl;
$R_6$ is H, —CH$_2$CH$_2$COOH, —CH$_2$C$_2$COOR or —COOH;
$R_7$ is —CH$_2$CH$_2$COOH, —CH$_2$CH$_2$COOR or $$\begin{bmatrix} -CH_2CH_2COOH; \\ -H \end{bmatrix}$$

$R_8$ is methyl or $$\begin{bmatrix} -CH_3; \\ -H \end{bmatrix}$$

$R_9$ is H, —COOH, —CH$_2$COOH or methyl;
provided that when $R_1$, $R_2$, $R_3$, $R_4$, $R_7$ and $R_8$ represent two substituents or are divalent and attached to the same carbon, the respective pyrrole ring to which attached is a dihydropyrrole;
R is lower alkyl or benzyl;
$R_6$ and $R_9$, taken together are $$\begin{matrix} -C=O & \text{or} & -C=O \\ | & & | \\ -CH_2 & & -CHCO_2CH_3 \end{matrix};$$

with the proviso that at least one of $R_1$ to $R_9$ is a free carboxyl group.

DETAILED DESCRIPTION OF THE INVENTION

All the medical agents used in the present invention are fluorescent compounds, which are represented by the foregoing general formula. The tetrapyrrole carboxylic acid has at least one and preferably three carboxyl groups and it is desirable that the carboxyl groups are connected asymmetrically. For example, the carboxylic acid groups are present on the rings A and B side of the molecule or on the rings C and D side of the molecule.

Also included in the compounds of the present invention are di- and tetrahydro-tetrapyrrole carboxylic acids which correspond to the above tetrapyrrole. Furthermore, pharmaceutically acceptable salts of the carboxyl groups of these carboxylic acids such as the salts of alkali metals, alkaline earth metals, ammonium and amines are included.

Furthermore, the compounds which is used in the present invention are mono-, di- and polyamides of amino monocarboxylic acids with the above tetrapyrrole carboxylic acids. Another usable groups of compounds are mono-, di- and polyamides of amino dicarboxylic acids with the same tetrapyrrole carboxylic acids as above. Furthermore, pharmaceutically acceptable salts of the carboxyl groups of these mono-, di or polyamides such as the salts of alkali metals, alkaline earth metals, ammonium and amines are included.

The above amino monocarboxylic acids which forms mono-, di- or polyamide by connecting with the above tetrapyrrole carboxylic acid by way of amide bonds are exemplified by serine, glycine, α-alanine, β-alanine, ε-amino-n-caproic acid, piperidine-2-carboxylic acid, piperidine-6-carboxylic acid, pyrrole-2-carboxylic acid, piperidine-6-propionic acid, pyrrole-5-acetic acid, and similar such acids. The preferred amino monocarboxylic acids are naturally occurring α-amino monocarboxylic acids, e.g., serine, alanine and glycine, which are readily available and provide the best results.

Exemplified as amino dicarboxylic acids are α-aminosuccinic acid (aspartic acid), α-aminoglutaric acid (glutamic acid), β-aminoglutaric acid, β-aminosebacic acid, 2,6-piperidine dicarboxylic acid, 2,5-pyrrole dicarboxylic acid, 2-carboxypyrrole-5-acetic acid, 2-carboxypiperidine-6-propionic acid, α-aminoadipic acid, and α-aminoazelaic acid. The preferred amino dicarboxylic acids are the naturally occurring α-amino dicarboxylic acids such as aspartic acid and glutamic acid. These compounds are easily available and produce best results.

The especially preferable tetrapyrrole compounds used in the present invention are represented by the following general formula.

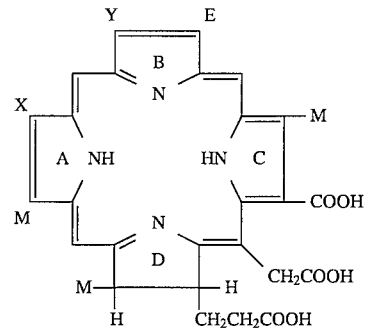

wherein, X is H, vinyl, ethyl, acetyl or formyl; Y is methyl or formyl; M is methyl; and E is ethyl.

Typical compounds of the tetrapyrrole classes are shown in Tables 1 and 2 in which the numbered positions of the tetrapyrrole ring structure are used to designate the position of the indicated substituent. The absence of double bonds in the ring system is designated under "dihydro" with each set of numbers (ring position) indicating the absence of a double bond between designated positions.

TABLE 1

| Porphyrin | Ring Position | | | | | | | | | Dihydro |
|---|---|---|---|---|---|---|---|---|---|---|
| | A | | B | | C | | | D | | |
| | 1 | 2 | 6 | 7 | 11 | 12 | 14 | 16 | 17 | |
| Coproporphyrin III | Me | Pr | Me | Pr | Me | Pr | H | Pr | Me | — |
| Deuteroporphyrin IX | Me | H | Me | H | Me | Pr | H | Pr | Me | — |
| Hematoporphyrin IX | Me | Me<br>\|<br>—CH<br>\|<br>OH | Me | Me<br>\|<br>—CH<br>\|<br>OH | Me | Pr | H | Pr | Me | — |
| Protoporphyrin IX | Me | V | Me | V | Me | Pr | H | Pr | Me | — |
| Photoprotoporphyrin IX (one of two isomers shown) | Me | V | { —Me<br>  —OH | =CHCHO | Me | Pr | H | Pr | Me | 6,7 |
| Mesoporphyrin IX | Me | Et | Me | Et | Me | Pr | H | Pr | Me | — |
| Transmesochlorin IX | { Me<br>  H | { Et<br>  H | Me | Et | Me | Pr | H | Pr | me | 1,2 |
| Transmesochlorin IX | Me | Et | { H<br>  Me | { H<br>  Et | Me | Pr | H | Pr | Me | 6,7 |
| Chlorin $e_4$ | Me | V | Me | Et | Me | $CO_2H$ | Me | { H<br>  Pr | { H<br>  Me | 16,17 |
| Chlorin $e_6$ | Me | V | Me | Et | Me | $CO_2H$ | Ac | { H<br>  Pr | { H<br>  Me | 16,17 |
| Mesochlorin $e_4$ | Me | Et | Me | Et | Me | $CO_2H$ | Me | { H<br>  Pr | { H<br>  Me | 16,17 |
| Isochlorin $e_4$ | Me | V | Me | Et | Me | H | Ac | { H<br>  Pr | { H<br>  Me | 16,17 |

TABLE 2

| Porphyrin | Ring Position | | | | | | | | | Dihydro |
|---|---|---|---|---|---|---|---|---|---|---|
| | A | | B | | C | | | D | | |
| | 1 | 2 | 6 | 7 | 11 | 12 | 14 | 16 | 17 | |
| Mesoisochlorin $e_4$ | Me | Et | Me | Et | Me | H | Ac | { H<br>  Pr | { H<br>  Me | 16,17 |
| Mesochlorin $e_6$ | Me | Et | Me | Et | Me | $CO_2H$ | Ac | { H<br>  Pr | { H<br>  Me | 16,17 |
| Bacteriochlorin $e_6$ | Me | ACL | { H<br>  Me | { H<br>  Et | Me | $CO_2H$ | Ac | { H<br>  Pr | { H<br>  Me | 6,7<br>16,17 |
| Bacteriochlorin $e_4$ | Me | ACL | { H<br>  Me | { H<br>  Et | Me | $CO_2H$ | Me | { H<br>  Pr | { H<br>  Me | 6,7<br>16,17 |
| Bacterioisochlorin $e_4$ | Me | ACL | { H<br>  Me | { H<br>  H | Me | H | Ac | { H<br>  Pr | { H<br>  Me | 6,7<br>16,17 |
| 2-Desvinylchlorin $e^6$ (or Deuterochlorin $e_6$) | Me | H | Me | Et | Me | $CO_2H$ | Ac | { H<br>  Pr | { H<br>  Me | 16,17 |
| 2-Acetylchlorin $e_6$ | Me | ACL | Me | Et | Me | $CO_2H$ | Ac | { H<br>  Pr | { H<br>  Me | 16,17 |
| 2-Formylchlorin $e_6$ | Me | CHO | Me | Et | Me | $CO_2H$ | Ac | { H<br>  Pr | { H<br>  Me | 16,17 |

Notes:
Me: —$CH_3$ (Methyl group)
Et: —$CH_2CH_3$ (Ethyl group)
Pr: —$CH_2CH_2COOH$ (Propionic acid group)
Ac: —$CH_2COOH$ (Acetic acid group)

TABLE 2-continued

| | Ring Position | | | | | | | | |
|---|---|---|---|---|---|---|---|---|---|
| | A | | B | | C | | D | | |
| Porphyrin | 1 | 2 | 6 | 7 | 11 | 12 | 14 | 16 | 17 | Dihydro |

V: —CH=CH$_2$ (Vinyl group)
ACL: CH$_3$—CO— (Acetyl group)

The amides used as the diagnosistic or therapeutic agents according to the present invention are exemplified in the following. In the first place, the amides with amino monocarboxylic acids are exemplified.

Chlorin Derivatives:
  (D,L)-Serinyl-trans-mesochlorin IX
  Glycyl-trans-mesochlorin IX
  α-(D,L)-Alanyl-trans-mesochlorin IX
  β-Alanyl-trans-mesochlorin IX
  ε-Amino-n-caproyl-mesochlorin IX
  (D,L)-Serinyl chlorine$_6$
  (D,L)-Serinyl mesochlorin e$_6$
  Glycyl chlorine$_6$
  Glycyl mesochlorin e$_6$
  α-(D,L)-Alanyl chlorine$_6$
  α-(D,L)-Alanyl mesochlorin e$_6$
  β-Alanyl chlorine$_6$
  β-Alanyl mesochlorin e$_6$
  ε-Amino-n-caproyl chlorine$_6$
  ε-Amino-n-caproyl mesochlorin e$_6$
  (D,L)-Serinyl chlorine$_4$
  (D,L)-Serinyl mesochlorin e$_4$
  (D,L)-Serinyl isochlorin e$_4$
  (D,L)-Serinyl mesoisochlorin e$_4$
  Glycyl chlorine$_4$
  Glycyl mesochlorin e$_4$
  Glycyl isochlorin e$_4$
  Glycyl mesoisochlorin e$_4$
  α-(D,L)-Alanyl chlorine$_4$
  α-(D,L)-Alanyl mesochlorin e$_4$
  α-(D,L)-Alanyl isochlorin e$_4$
  α-(D,L)-Alanyl mesoisochlorin e$_4$
  β-Alanyl chlorine$_4$
  β-Alanyl mesochlorin e$_4$
  β-Alanyl isochlorin e$_4$
  ε-Alanyl mesoisochlorin e$_4$
  ε-Amino-n-caproyl chlorine$_4$
  ε-Amino-n-caproyl mesochlorin e$_4$
  ε-Amino-n-caproyl isochlorin e$_4$
  ε-Amino-n-caproyl mesoisochlorin e$_4$
  (D,L)-Serinyl pyropheophorbide a
  Glycyl pyropheophorbide a
  α-(D,L)-Alanyl pyropheophorbide a
  β-Alanyl pyropheophorbide a
  ε-Amino-n-caproyl pyropheophorbide a
  (D,L)-Serinyl pheophorbide a
  Glycyl pheophorbide a
  α-(D,L)-Alanyl pheophorbide a
  β-Alanyl pheophorbide a
  ε-Amino-n-caproyl pheophorbide a
  (D,L)-Serinyl photoprotoporphyrin IX
  Glycyl photoprotoporphyrin IX
  α-(D,L)-Alanyl-photoprotoporphyrin IX
  β-Alanyl photoprotoporphyrin IX
  ε-Amino-n-caproyl photoprotoporphyrin IX
  Threoninyl chlorine$_6$
  Tyrosyl chlorine$_6$
  Valyl chlorine$_6$
  Leucyl chlorine$_6$
  Isoleucyl chlorine$_6$
  Prolyl chlorine$_6$
  Methionyl chlorine$_6$
  Histidyl chlorine$_6$
  Arginyl chlorine$_6$
  Lysyl chlorine$_6$
  Glutaminyl chlorine$_6$
  4-Hydroxyprolyl chlorine$_6$
  5-Hydroxylysyl chlorine$_6$
  ε-Amino-n-caproyl chlorine$_6$
  γ-Aminobutanoyl chlorine$_6$
  3-Methyl histidyl chlorine$_6$
  Alanyl-2-acetyl chlorine$_6$
  Valyl-2-acetyl chlorine$_6$
  Leucyl-2-acetyl chlorine$_6$
  Isoleucyl-2-acetyl chlorine$_6$
  prolyl-2-acetyl chlorine$_6$
  Methionyl-2-acetyl chlorine$_6$
  Glycyl-2-acetyl chlorine$_6$
  Serinyl-2-acetyl chlorine$_6$
  Threoninyl-2-acetyl chlorine$_6$
  Cysteinyl-2-acetyl chlorine$_6$
  Tyrosyl-2-acetyl chlorine$_6$
  Asparginyl-2-acetyl chlorine$_6$
  Lysyl-2-acetyl chlorine$_6$
  Arginyl-2-acetyl chlorine$_6$
  Histidyl-2-acetyl chlorine$_6$
  Glutaminyl-2-acetyl chlorine$_6$
  4-Hydroxyprolyl-2-acetyl chlorine$_6$
  5-Hydroxylysyl-2-acetyl chlorine$_6$
  ε-Amino-n-caproyl-2-acetyl chlorine$_6$
  γ-Aminobutanoyl-2-acetyl chlorine$_6$
  3-Methyl histidyl-2-acetyl chlorine$_6$
  β-Alanyl-2-acetyl chlorine$_6$
  Alanyl-2-formyl chlorine$_6$
  Valyl-2-formyl chlorine$_6$
  Leucyl-2-formyl chlorine$_6$
  Isoleucyl-2-formyl chlorine$_6$
  Prolyl-2-formyl chlorine$_6$
  Methionyl-2-formyl chlorine$_6$
  Glycyl-2-formyl chlorine$_6$
  Serinyl-2-formyl chlorine$_6$
  Threoninyl-2-formyl chlorine$_6$
  Cysteinyl-2-formyl chlorine$_6$
  Tyrosyl-2-formyl chlorine$_6$
  Asparginyl-2-formyl chlorine$_6$
  Lysyl-2-formyl chlorine$_6$
  Arginyl-2-formyl chlorine$_6$
  Histidyl-2-formyl chlorine$_6$
  Glutaminyl-2-formyl chlorine$_6$
  4-Hydroxyprolyl-2-formyl chlorine$_6$
  5-Hydroxylysyl-2-formyl chlorine$_6$
  ε-Amino-n-caproyl-2-formyl chlorine$_6$
  γ-Aminobutanoyl-2-formyl chlorine$_6$
  3-Methyl histidyl-2-formyl chlorine$_6$ β-Alanyl-2-formyl chlorine$_6$
Alanyl deuterochlorin e$_6$
Valyl deuterochlorin e$_6$
Leucyl deuterochlorin e$_6$
Isoleucyl deuterochlorin e$_6$
Prolyl deuterochlorin e$_6$
Methionyl deuterochlorin e$_6$
Glycyl deuterochlorin e$_6$
Serinyl deuterochlorin e$_6$
Threoninyl deuterochlorin e$_6$
Cysteinyl deuterochlorin e$_6$
Tyrosyl deuterochlorin e$_6$
Asparginyl deuterochlorin e$_6$
Lysyl deuterochlorin e$_6$
Arginyl deuterochlorin e$_6$
Histidyl deuterochlorin e$_6$
Glutaminyl deuterochlorin e$_6$
4-Hydroxyprolyl deuterochlorin e$_6$
5-Hydroxylysyl deuterochlorin e$_6$
6-Amino-n-caproyl deuterochlorin e$_6$
γ-Aminobutanoyl deuterochlorin e$_6$
3-Methyl histidyl deuterochlorin e$_6$
β-Alanyl deuterochlorin e$_6$
Valyl mesochlorin e$_6$
Leucyl mesochlorin e$_6$
Isoleucyl mesochlorin e$_6$
Prolyl mesochlorin e$_6$
Methionyl mesochlorin e$_6$
Serinyl mesochlorin e$_6$
Threoninyl mesochlorin e$_6$
Cysteinyl mesochlorin e$_6$
Tyrosyl mesochlorin e$_6$
Asparginyl mesochlorin e$_6$
Lysyl mesochlorin e$_6$
Arginyl mesochlorin e$_6$
Histidyl mesochlorin e$_6$
Glutaminyl mesochlorin e$_6$
4-Hydroxyprolyl mesochlorin e$_6$
5-Hydroxylysyl mesochlorin e$_6$
γ-Aminobutanoyl mesochlorin e$_6$
3-Methyl histidyl mesochlorin e$_6$
Porphyrin Derivatives:
  (D,L)-Serinyl mesoporphyrin IX
  Glycyl mesoporphyrin IX
  α-(D,L)-Alanyl mesoporphyrin IX
  β-Alanyl mesoporphyrin IX
  ε-Amino-n-caproyl mesoporphyrin IX
  (D,L)-Serinyl protoporphyrin IX
  Glycyl protoporphyrin IX
  α-(D,L)-Alanyl protoporphyrin IX
  β-Alanyl protoporphyrin IX
  ε-Amino-n-caproyl protoporphyrin IX
  (D,L)-Serinyl deuteroporphyrin IX
  Glycyl deuteroporphyrin IX
  α-(D,L)-Alanyl deuteroporphyrin IX
  β-Alanyl deuteroporphyrin IX
  ε-Amino-n-caproyl deuteroporphyrin IX
  (D,L)-Serinyl coproporphyrin III
  Glycyl coproporphyrin III
  α-(D,L)-Alanyl coproporphyrin III
  β-Alanyl coproporphyrin III
  ε-Amino-n-caproyl coproporphyrin III
  (D,L)-Serinyl hematoporphyrin IX
  Glycyl hematoporphyrin IX
  α-(D,L)-Alanyl hematoporphyrin IX
  β-Alanyl hematoporphyrin IX
  ε-Amino-n-caproyl hematoporphyrin IX Bacteriochlorin Derivatives:
  (D,L)-Serinyl bacteriochlorin e$_4$
  Glycyl bacteriochlorin e$_4$
  α-(D,L)-Alanyl bacteriochlorin e$_4$
  β-Alanyl bacteriochlorin e$_4$
  ε-Amino-n-caproyl bacteriochlorin e$_4$
  (D,L)-Serinyl bacterioisochlorin e$_4$
  Glycyl bacterioisochlorin e$_4$
  α-(D,L)-Alanyl bacterioisochlorin e$_4$
  β-Alanyl bacterioisochlorin e$_4$
  ε-Amino-n-caproyl bacterioisochlorin e$_4$
  (D,L)-Serinyl bacteriochlorin e$_6$
  Glycyl bacteriochlorin e$_6$
  α-(D,L)-Alanyl bacteriochlorin e$_6$
  β-Alanyl bacteriochlorin e$_6$
  ε-Amino-n-caproyl bacteriochlorin e$_6$
  (D,L)-Serinyl pyrobacteriopheophorbide a
  Glycyl pyrobacteriopheophorbide a
  α-(D,L)-Alanyl pyrobacteriopheophorbide a
  β-Alanyl pyrobacteriopheophorbide a
  ε-Amino-n-caproyl pyrobacteriopheophorbide a
  (D,L)-Serinyl bacteriopheophorbide a
  Glycyl bacteriopheophorbide a
  α-(D,L)-Alanyl bacteriopheophorbide a
  β-Alanyl bacteriopheophorbide a
  ε-Amino-n-caproyl bacteriopheophorbide a In the following, di- or polyamides of amino monocarboxylic acids are further exemplified,
Chlorin Derivatives:
  Di-(D,L)-serinyl-trans-mesochlorin IX
  Di-glycyl-trans-mesochlorin IX
  Di-α-(D,L)-alanyl-trans-mesochlorin IX
  Di-β-alanyl-trans-mesochlorin IX
  Di-ε-amino-n-caproyl-mesochlorin IX
  Di, tri-(D,L)-serinyl chlorine$_6$
  Di, tri-(D,L)-serinyl mesochlorin e$_6$
  Di, tri-glycyl chlorine$_6$
  Di, tri-glycyl mesochlorin e$_6$
  Di, tri-α-(D,L)-alanyl chlorine$_6$
  Di, tri-α-(D,L)-alanyl mesochlorin e$_6$
  Di, tri-β-alanyl chlorine$_6$
  Di, tri-β-alanyl mesochlorin e$_6$
  Di, tri-ε-amino-n-caproyl chlorine$_6$
  Di, tri-ε-amino-n-caproyl mesochlorin e$_6$
  Di-(D,L)-serinyl chlorine$_4$
  Di-(D,L)-serinyl mesochlorin e$_4$
  Di-(D,L)-serinyl isochlorin e$_4$
  Di-(D,L)-serinyl mesoisochlorin e$_4$
  Di-glycyl chlorine$_4$
  Di-glycyl mesochlorin e$_4$
  Di-Olycyl isochlorin e$_4$
  Di-glycyl mesoisochlorin e$_4$
  Di-α-(D,L)-alanyl chlorine$_4$
  Di-α-(D,L)-alanyl mesochlorin e$_4$
  Di-α-(D,L)-alanyl isochlorin e$_4$
  Di-α-(D,L)-alanyl mesoisochlorin e$_4$
  Di-β-alanyl chlorine$_4$
  Di-β-alanyl mesochlorin e$_4$
  Di-β-alanyl isochlorin e$_4$
  Di-β-alanyl mesoisochlorin e$_4$
  Di-ε-amino-n-caproyl chlorine$_4$
  Di-ε-amino-n-caproyl mesochlorin e$_4$
  Di-ε-amino-n-caproyl isochlorin e$_4$
  Di-ε-amino-n-caproyl mesoisochlorin e$_4$
  Di-(D,L)-serinyl photoprotoporphyrin IX
  Di-glycyl photoprotoporphyrin IX
  Di-α-(D,L)-alanyl-photoprotoporphyrin IX Di-β-alanyl photoprotoporphyrin IX
Di-ε-amino-n-caproyl photoprotoporphyrin IX
Porphyrin Derivatives:
  Di-(D,L)-serinyl mesoporphyrin IX
  Di-glycyl mesoporphyrin IX
  Di-α-(D,L)-alanyl mesoporphyrin IX
  Di-β-alanyl mesoporphyrin IX
  Di-ε-amino-n-caproyl mesoporphyrin IX
  Di-(D,L)-serinyl protoporphyrin IX
  Di-glycyl protoporphyrin IX
  Di-α-(D,L)-alanyl protoporphyrin IX
  Di-β-alanyl protoporphyrin IX
  Di-ε-amino-n-caproyl protoporphyrin IX
  Di-(D,L)-serinyl deuteroporphyrin IX
  Di-glycyl deuteroporphyrin IX
  Di-α-(D,L)-alanyl deuteroporphyrin IX
  Di-β-alanyl deuteroporphyrin IX
  Di-ε-amino-n-caproyl deuteroporphyrin IX
  Di, tri, tetra-(D,L)-serinyl coproporphyrin III
  Di, tri, tetra-glycyl coproporphyrin III
  Di, tri, tetra-α-(D,L)-alanyl coproporphyrin III
  Di, tri, tetra-β-alanyl coproporphyrin III
  Di, tri, tetra-ε-amino-n-caproyl coproporphyrin III
  Di-(D,L)-serinyl hematoporphyrin IX
  Di-glycyl hematoporphyrin IX
  Di-α-(D,L)-alanyl hematoporphyrin IX
  Di-β-alanyl hematoporphyrin IX
  Di-ε-amino-n-caproyl hematoporphyrin IX
Bacteriochlorin Derivatives:
  Di-(D,L)-serinyl bacteriochlorin $e_4$
  Di-glycyl bacteriochlorin $e_4$
  Di-α-(D,L)-alanyl bacteriochlorin $e_4$
  Di-β-alanyl bacteriochlorin $e_4$
  Di-ε-amino-n-caproyl bacteriochlorin $e_4$
  Di-(D,L)-serinyl bacterioisochlorin $e_4$
  Di-glycyl bacterioisochlorin $e_4$
  Di-α-(D,L)-alanyl bacterioisochlorin $e_4$
  Di-β-alanyl bacterioisochlorin $e_4$
  Di-ε-amino-n-caproyl bacterioisochlorin $e_4$
  Di, tri-(D,L)-serinyl bacteriochlorin $e_6$
  Di, tri-glycyl bacteriochlorin $e_6$
  Di, tri-α-(D,L)-alanyl bacteriochlorin $e_6$
  Di, tri-β-alanyl bacteriochlorin $e_6$
  Di, tri-ε-amino-n-caproyl bacteriochlorin $e_6$ Similarly, using other amino acids, the following amides can be employed, however, they do not limit the present invention.

Di-threoninyl trans-mesochlorin IX
  Di, tri-threoninyl chlorine$_6$
  Di, tri-threoninyl mesochlorin $e_6$
  Di-threoninyl chlorine$_4$
  Di-threoninyl mesochlorin $e_4$
  Di-threoninyl isochlorin $e_4$
  Di-threoninyl mesoisochlorin $e_4$
  Di-threoninyl photoprotoporphyrin IX
  Di-threoninyl mesoporphyrin IX
  Di-threoninyl protoporphyrin IX
  Di-threoninyl deuteroporphyrin IX
  Di, tri, tetra-threoninyl coproporphyrin III
  Di-threoninyl hematoporphyrin IX
  Di-threoninyl bacteriochlorin $e_4$
  Di-threoninyl bacterioisochlorin $e_4$
  Di, tri-threoninyl bacteriochlorin $e_6$
  Di-cysteinyl trans-mesochlorin IX
  Di, tri-cysteinyl chlorine$_6$
  Di, tri-cysteinyl mesochlorin $e_6$
  Di-cysteinyl chlorine$_4$
  Di-cysteinyl mesochlorin $e_4$
  Di-cysteinyl isochlorin $e_4$
  Di-cysteinyl mesoisochlorin $e_4$
  Di-cysteinyl photoprotoporphyrin IX
  Di-cysteinyl mesoporphyrin IX
  Di-cysteinyl protoporphyrin IX
  Di-cysteinyl deuteroporphyrin IX
  Di, tri, tetra-cysteinyl coproporphyrin III
  Di-cysteinyl hematoporphyrin IX
  Di-cysteinyl bacteriochlorin $e_4$
  Di-cysteinyl bacterioisochlorin $e_4$
  Di, tri-cysteinyl bacteriochlorin $e_6$
  Di-tyrosyl trans-mesochlorin IX
  Di, tri-tyrosyl chlorine$_6$
  Di, tri-tyrosyl mesochlorin $e_6$
  Di-tyrosyl chlorine$_4$
  Di-tyrosyl mesochlorin $e_4$
  Di-tyrosyl isochlorin $e_4$
  Di-tyrosyl mesoisochlorin $e_4$
  Di-tyrosyl photoprotoporphyrin IX
  Di-tyrosyl mesoporphyrin IX
  Di-tyrosyl protoporphyrin IX
  Di-tyrosyl deuteroporphyrin IX
  Di, tri, tetra-tyrosyl coproporphyrin
  Di-tyrosyl hematoporphyrin IX
  Di-tyrosyl bacteriochlorin $e_4$
  Di-tyrosyl bacterioisochlorin $e_4$
  Di, tri-tyrosyl bacteriochlorin $e_6$
  Di-valyl trans-mesochlorin IX
  Di, tri-valyl chlorine$_6$
  Di, tri-valyl mesochlorin $e_6$
  Di-valyl chlorine$_4$
  Di-valyl mesochlorin $e_4$
  Di-valyl isochlorin $e_4$
  Di-valyl mesoisochlorin $e_4$
  Di-valyl photoprotoporphyrin IX
  Di-valyl mesoporphyrin IX
  Di-valyl protoporphyrin IX
  Di-valyl deuteroporphyrin IX
  Di, tri, tetra-valyl coproporphyrin III
  Di-valyl hematoporphyrin IX
  Di-valyl bacteriochlorin $e_4$
  Di-valyl bacterioisochlorin $e_4$
  Di, tri-valyl bacteriochlorin $e_6$
  Di-leucyl trans-mesochlorin IX
  Di, tri-leucyl chlorine$_6$
  Di, tri-leucyl mesochlorin $e_6$
  Di-leucyl chlorine$_4$
  Di-leucyl mesochlorin $e_4$
  Di-leucyl isochlorin $e_4$
  Di-leucyl mesoisochlorin $e_4$
  Di-leucyl photoprotoporphyrin IX
  Di-leucyl mesoporphyrin IX
  Di-leucyl protoporphyrin IX
  Di-leucyl deuteroporphyrin IX
  Di, tri, tetra-leucyl coproporphyrin III
  Di-leucyl hematoporphyrin IX
  Di-leucyl bacteriochlorin $e_4$
  Di-leucyl bacterioisochlorin $e_4$
  Di, tri-leucyl bacteriochlorin $e_6$
  Di-isoleucyl trans-mesochlorin IX
  Di, tri-isoleucyl chlorine$_6$
  Di, tri-isoleucyl mesochlorin $e_6$
  Di-isoleucyl chlorine$_4$
  Di-isoleucyl mesochlorin $e_4$
  Di-isoleucyl isochlorin $e_4$
  Di-isoleucyl mesoisochlorin $e_4$ Di-isoleucyl photoprotoporphyrin IX
Di-isoleucyl mesoporphyrin IX
Di-isoleucyl protoporphyrin IX
Di-isoleucyl deuteroporphyrin IX
Di, tri, tetra-isoleucyl coproporphyrin III
Di-isoleucyl hematoporphyrin IX
Di-isoleucyl bacteriochlorin $e_4$
Di-isoleucyl bacterioisochlorin $e_4$
Di, tri-isoleucyl bacteriochlorin $e_6$
Di-prolyl trans-mesochlorin IX
Di, tri-prolyl chlorine$_6$
Di, tri-prolyl mesochlorin $e_6$
Di-prolyl chlorine$_4$
Di-prolyl mesochlorin $e_4$
Di-prolyl isochlorin $e_4$
Di-prolyl mesoisochlorin $e_4$
Di-prolyl photoprotoporphyrin IX
Di-prolyl mesoporphyrin IX
Di-prolyl protoporphyrin IX
Di-prolyl deuteroporphyrin IX
Di, tri, tetra-prolyl coproporphyrin III
Di-prolyl hematoporphyrin IX
Di-prolyl bacteriochlorin $e_4$
Di-prolyl bacterioisochlorin $e_4$
Di, tri-prolyl bacteriochlorin $e_6$
Di-phenylalanyl trans-mesochlorin IX
Di, tri-phenylalanyl chlorine$_6$
Di, tri-phenylalanyl mesochlorin $e_6$
Di-phenylalanyl chlorine$_4$
Di-phenylalanyl mesochlorin $e_4$
Di-phenylalanyl isochlorin $e_4$
Di-phenylalanyl mesoisochlorin $e_4$
Di-phenylalanyl photoprotoporphyrin IX
Di-phenylalanyl mesoporphyrin IX
Di-phenylalanyl protoporphyrin IX
Di-phenylalanyl deuteroporphyrin IX
Di, tri, tetra-phenylalanyl coproporphyrin III
Di-phenylalanyl hematoporphyrin IX
Di-phenylalanyl bacteriochlorin $e_4$
Di-phenylalanyl bacterioisochlorin $e_4$
Di, tri-phenylalanyl bacteriochlorin $e_6$
Di-tryptophyl trans-mesochlorin IX
Di, tri-tryptophyl chlorine$_6$
Di, tri-tryptophyl mesochlorin $e_6$
Di-tryptophyl chlorine$_4$
Di-tryptophyl mesochlorin $e_4$
Di-tryptophyl isochlorin $e_4$
Di-tryptophyl mesoisochlorin $e_4$
Di-tryptophyl photoprotoporphyrin IX
Di-tryptophyl mesoporphyrin IX
Di-tryptophyl protoporphyrin IX
Di-tryptophyl deuteroporphyrin IX
Di, tri, tetra-tryptophyl coproporphyrin III
Di-tryptophyl hematoporphyrin IX
Di-tryptophyl bacteriochlorin $e_4$
Di-tryptophyl bacterioisochlorin $e_4$
Di, tri-tryptophyl bacteriochlorin $e_6$
Di-methionyl trans-mesochlorin IX
Di, tri-methionyl chlorine$_6$
Di, tri-methionyl mesochlorin $e_6$
Di-methionyl chlorine$_4$
Di-methionyl mesochlorin $e_4$
Di-methionyl isochlorin $e_4$
Di-methionyl mesoisochlorin $e_4$
Di-methionyl photoprotoporphyrin IX
Di-methionyl mesoporphyrin IX
Di-methionyl protoporphyrin IX
Di-methionyl deuteroporphyrin IX
Di, tri, tetra-methionyl coproporphyrin III
Di-methionyl hematoporphyrin IX
Di-methionyl bacteriochlorin $e_4$
Di-methionyl bacterioisochlorin $e_4$
Di, tri-methionyl bacteriochlorin $e_6$
Di-histidyl trans-mesochlorin IX
Di, tri-histidyl chlorin $e_6$
Di, tri-histidyl mesochlorin $e_6$
Di-histidyl chlorine$_4$
Di-histidyl mesochlorin $e_4$
Di-histidyl isochlorin $e_4$
Di-histidyl mesoisochlorin $e_4$
Di-histidyl photoprotoporphyrin IX
Di-histidyl mesoporphyrin IX
Di-histidyl protoporphyrin IX
Di-histidyl deuteroporphyrin IX
Di, tri, tetra-histidyl coproporphyrin III
Di-histidyl hematoporphyrin IX
Di-histidyl bacteriochlorin $e_4$
Di-histidyl bacterioisochlorin $e_4$
Di, tri-histidyl bacteriochlorin $e_6$
Di-arginyl trans-mesochlorin IX
Di, tri-arginyl chlorine$_6$
Di, tri-arginyl mesochlorin $e_6$
Di-arginyl chlorine$_4$
Di-arginyl mesochlorin $e_4$
Di-arginyl isochlorin $e_4$
Di-arginyl mesoisochlorin $e_4$
Di-arginyl photoprotoporphyrin IX
Di-arginyl mesoporphyrin IX
Di-arginyl protoporphyrin IX
Di-arginyl deuteroporphyrin IX
Di, tri, tetra-arginyl coproporphyrin III
Di-arginyl hematoporphyrin IX
Di-arginyl bacteriochlorin $e_4$
Di-arginyl bacterioisochlorin $e_4$
Di, tri-arginyl bacteriochlorin $e_6$
Di-lysyl trans-mesochlorin IX
Di, tri-lysyl chlorine$_6$
Di, tri-lysyl mesochlorin $e_6$
Di-lysyl chlorine$_4$
Di-lysyl mesochlorin $e_4$
Di-lysyl isochlorin $e_4$
Di-lysyl mesoisochlorin $e_4$
Di-lysyl photoprotoporphyrin IX
Di-lysyl mesoporphyrin IX
Di-lysyl protoporphyrin IX
Di-lysyl deuteroporphyrin IX
Di, tri, tetra-lysyl coproporphyrin III
Di-lysyl hematoporphyrin IX
Di-lysyl bacteriochlorin $e_4$
Di-lysyl bacterioisochlorin $e_4$
Di, tri-lysyl bacteriochlorin $e_6$
Di-glutaminyl trans-mesochlorin IX
Di, tri-glutaminyl chlorine$_6$
Di, tri-glutaminyl mesochlorin $e_6$
Di-Olutaminyl chlorine$_4$
Di-glutaminyl mesochlorin $e_4$
Di-glutaminyl isochlorin $e_4$
Di-glutaminyl mesoisochlorin $e_4$
Di-glutaminyl photoprotoporphyrin IX
Di-glutaminyl mesoporphyrin IX
Di-glutaminyl protoporphyrin IX
Di-glutaminyl deuteroporphyrin IX
Di, tri, tetra-glutaminyl coproporphyrin III
Di-glutaminyl hematoporphyrin IX Di-glutaminyl bacteriochlorin $e_4$
Di-glutaminyl bacterioisochlorin $e_4$
Di, tri-glutaminyl bacteriochlorin $e_6$
Di-asparginyl trans-mesochlorin IX
Di, tri-asparginyl chlorine$_6$
Di, tri-asparginyl mesochlorin $e_6$
Di-asparginyl chlorine$_4$
Di-asparginyl mesochlorin $e_4$
Di-asparginyl isochlorin $e_4$
Di-asparginyl mesoisochlorin $e_4$
Di-asparginyl photoprotoporphyrin IX
Di-asparginyl mesoporphyrin IX
Di-asparginyl protoporphyrin IX
Di-asparginyl deuteroporphyrin IX
Di, tri, tetra-asparginyl coproporphyrin III
Di-asparginyl hematoporphyrin IX
Di-asparginyl bacteriochlorin $e_4$
Di-asparginyl bacterioisochlorin $e_4$
Di, tri-asparginyl bacteriochlorin $e_6$ In the following, mono-, di- or polyamides of amino dicarboxylic acids are exemplified.

Chlorin Derivatives:
  Mono and diaspartyl trans-mesochlorin IX
  Mono and diglutamyl trans-mesochlorin IX
  Mono, di and triaspartyl chlorine$_6$
  Mono, di and triaspartyl mesochlorin $e_6$
  Mono, di and triglutamyl chlorine$_6$
  Mono, di and triglutamyl mesochlorin $e_6$
  Mono and diaspartyl chlorine$_4$
  Mono and diaspartyl mesochlorin $e_4$
  Mono and diaspartyl isochlorin $e_4$
  Mono and diaspartyl mesoisochlorin $e_4$
  Mono and diglutamyl chlorine$_4$
  Mono and diglutamyl mesochlorin $e_4$
  Mono and diglutamyl isochlorin $e_4$
  Mono and diglutamyl mesoisochlorin $e_4$
  Monoaspartyl pyropheophorbide a
  Monoglutamyl pyropheophorbide a
  Monoaspartyl pheophorbide a
  Monoglutamyl pheophorbide a
  Mono and diaspartyl photoprotoporphyrin IX
  Mono and diglutamyl photoprotoporphyrin IX
  Mono and di-L-a-aminoadipyl trans-mesochlorin IX Porphyrin Derivatives:
  Mono and diaspartyl mesoporphyrin IX
  Mono and diglutamyl mesoporphyrin IX
  Mono and diaspartyl protoporphyrin IX
  Mono and diglutamyl protoporphyrin IX
  Mono and diaspartyl deuteroporphyrin IX
  Mono and diglutamyl deuteroporphyrin IX
  Mono, di, tri and tetraaspartyl coproporphyrin III (isomer mixture)
  Mono, di, tri and tetraglutamyl coproporphyrin III
  Mono and diaspartyl hematoporphyrin IX
  Mono and diglutamyl hematoporphyrin IX Bacteriochlorin Derivatives:
  Mono and diaspartyl bacteriochlorin $e_4$
  Mono and diglutamyl bacteriochlorin $e_4$
  Mono and diaspartyl bacterioisochlorin $e_4$
  Mono and diglutamyl bacterioisochlorin $e_4$
  Mono, di and triaspartyl bacteriochlorin $e_6$
  Mono, di and triglutamyl bacteriochlorin $e_6$
  Monoaspartyl pyrobacteriopheophorbide a
  Monoglutamyl pyrobacteriopheophorbide a
  Monoaspartyl bacteriopheophorbide a
  Monoglutamyl bacteriopheophorbide a The tetrapyrrole compounds used in the present invention can be prepared by various synthetic methods which are found in the literatures. For example, the following literatures are exemplified with regard to chlorinc $e_6$.

(1) Willstatter, R. and Stoll, A.; "Investigations on Chlorophyll", (Trans.: Schertz, F. M., Merz, A. R.), p. 176, Science Printing Press, Lancaster, Pa., U.S.A., 1928.

(2) Willstatter, R. and Isler, M.; Ann. Chem., 390, 269 (1912).

The compounds employed in the present invention are useful for the photodynamic diagnosis and photodynamic therapy of rheumatoid arthritis. When a man or a mammal animal having rheumatoid arthritis is treated with doses of the above-mentioned compound, the compound is selectively accumulated in the arthritic lesion and when light rays of proper wavelength and intensity are applied to the lesion, the compound generates fluorescence and produces active oxygen. Thereby the arthritic lesion being diagnosed by inspecting the generated fluorescence and the affected lesion is cured by the cytotoxic effect of active oxygen.

The host of a living body to be dosed is a mammal having rheumatoid arthritis in its body.

The compounds used for the photodynamic diagnosis and photodynamic therapy should have the following properties:

(a) non-toxic at normal diagnostic or therapeutic dosage unless and until activated by light rays;

(b) should be accumulated selectively in arthritic lesions;

(c) should be selectively photoactive on specific wavelengths;

(d) when irradiated with light rays or electromagnetic waves, they generate detectable specific fluorescence;

(e) when irradiated with light rays or electromagnetic waves, they are activated to cytotoxic level in arthritic lesion; and (f) easily metabolized or excreted after the diagnosis and therapeutic treatment.

The foregoing compounds as the diagnostic or therapeutic agents used in the present invention must have the above properties and are also characterized by the reasonable solubility in water at physiological pH.

As compared with the use of conventional tetrapyrroles such as the foregoing hematoporphyrin derivative of Photofrin II, the above-described compounds generate fluorescence of greater intensity in arthritic lesions with the same quantities of doses. Accordingly, with the use of the above-mentioned compounds, the arthritic lesion provides more intense contrast as compared with the normal tissue around the arthritic lesion.

Furthermore, the intensity of fluorescence which is generated from some conventionally used tetrapyrroles varies or the fluorescence generated in the body of host varies from day to day, however, the intensity of fluorescence generated by the above compounds is quite stable.

The compounds used in the present invention absorb activation energy for the photodynamic diagnosis and photodynamic therapy in the range of 300 to 800 nm in wavelength, with the preferred compound absorbing in the 360 to 760 nm, i.e., the light of longer wavelength which more readily permits penetration of energy into the arthritic lesion for facilitating the purpose of photodynamic diagnosis and photodynamic therapy.

Incidentally, the specific wavelength of fluorescence which is emitted from the compound used in the present invention that is accumulated in the arthritic lesion is shifted by about 10 nm as compared with that of the same compound in a phosphate buffered saline solution. From this fact, it is considered that the compound used in the present invention is not physically caught simply within the arthritic lesion but it is connected to the lesion by some interconnection mechanism. When the wavelength is shifted, the change in the intensity of fluorescence is also caused to occur usually. However, in the case of the foregoing compounds, the intensity of fluorescence is not weakened but rather strengthened. Accordingly, the above-mentioned compounds are most suitable for the photodynamic diagnosis and photodynamic therapy.

According to the experience until now, the quantity of dosage can be reduced considerably because the above-mentioned compounds are uniformly distributed all around the arthritic lesion. Because the quantity of dosage can be reduced, it is possible to suppress the occurrence of photodynamic sensitization in a host even when the administered compound is not excreted.

The quantity of administration of the fore.going compound is determined depending on the purpose of dosage. FOr the purpose of diagnosis, a dosage of only 1 mg/kg (weight of living body) produces an effect for detection. The quantity is, however, generally up to about 5 mg/kg. The quantity of dosage for the therapeutic purpose is generally in the range of about 0.1 to 20 kg/mg. The quantity of the administration for diagnosis and therapy can be varied in a wide range in view of the above-mentioned advantage that the compound used in the present invention is liable to be excreted from a living body. The compound of the present invention is apparently innocuous with the dose for the above-described diagnostic and therapeutic purpose. For example, no test animal was killed owing to the compound used in the present invention in experiments with the doses up to 20 mg/kg.

A compound used in the present invention which is dissolved in an appropriate aqueous solution such as a phosphate buffered saline solution is administered by a proper method to the living body of a host to be diagnosed or treated. Besides the aqueous solution, it can be an aqueous dispersion containing a suitable dispersing agent. It is preferable that the medical compound is administered by a direct method such as intravenous injection. Meanwhile, the oral, intramuscular or hypodermic administration is also possible. It is also possible to administer the compound directly into the joint cavity. In any case, the solution of the above-mentioned compound may also contain the following known materials: a binder such as gum tragacanth; an excipient such as dicalcium phosphate; a disintegrating agent such as corn starch; a lubricant such as magnesium stearate; a sweetening agent such as sucrose; a preservative such as paraben; a dye; a flavoring such as cherry flavor; a solvent or dispersion medium such as water, ethanol or glycol; an antiseptic; and an isotonic agent such as sugar and sodium chloride.

These compounds can be prepared for use as preferable basic salts, for example, sodium salts in the form of lyophilized pyrogen-free sterile compounds. The preferable type of the medical agent is an isotonic solution usable for injection.

Although the reason has not been clear, the compounds used in the present invention are specifically and selectively accumulated in the arthritic lesion (hyperplastic synovial membrane) in a living body. Accordingly, after the passage of a proper time, for example, in several minutes to several hours after the administration into a vein, light rays are applied to the arthritic lesion.

The irradiation must be an amount sufficient to cause the compound to generate fluorescence for diagnosis and also to exert a cytotoxic effect for therapy. The light source for the irradiation in the photodynamic diagnosis and photodynamic therapy is not limited, however, a laser beam is generally used because an intense light ray within a desired wavelength range can be applied selectively.

Usable sources for the irradiation of laser beams are a strong continuous light source through a filter, an exited dye laser or other laser apparatus, and transmitted beam system. As described above, the wavelength of the laser beam is in the range of 360 to 760 nm. The intensity of irradiation is appropriately selected generally from the range of 10 to 1000 mW/cm$^2$ preferably 20 to 500 mW/cm$^2$. The capacity of the laser apparatus is at least 500 mW. Some of commercially available laser apparatus meets these requirements.

In the practice of photodynamic diagnosis, the above-mentioned compound is administered to the body of human or animal and, after a certain period of time, light rays are applied to the lesion to be inspected. When a arthroscope can be used for the lesion in elbow or knee joints, the irradiation is done using the arthroscope. The lesion of rheumatoid arthritis selectively generates fluorescence, which lesion can be observed directly by naked eyes or with an image on a CRT screen.

In the practice of photodynamic therapy, the laser beam irradiation is carried out from the tip end of a quartz fiber bundle after administering the compound. This can be done by inserting the tip end of quartz fiber bundle into the arthritic lesion as well as by irradiating the surface of arthritic lesion. The irradiated state is observed directly by naked eyes or with an image on a CRT screen.

The diagnosis and therapy using the foregoing medical agents can be applied to the diseases which causes the growth or inflammation of the synovial membrane in a joint cavity such as the diseases causing arthritis, diseases similar to rheumatoid arthritis or complications of rheumatoid arthritis. For example, the analogous diseases of juvenile rheumatoid arthritis, systemic lupus erythematosus, Reiter's syndrome, psoriatic arthritis, and pigmented villonodular synovitis.

In the following, the present invention is described in more detail with examples of medical effect tests concerning the above-mentioned medical compounds.

Photodynamic diagnosis and photodynamic therapy were carried out by administering the above-mentioned compounds to rats affected with adjuvant induced arthritis (herein after referred to as "A. A. rat". The A. A. rats had arthritic lesions which closely resemble the human rheumatoid arthritis in morphological and biochemical characteristics.

Mono-L-aspartyl chlorin $e_6$ (hereinafter referred to as "NPe6") was used as a test compound.

As a compound to be compared with, photofrin II (trademark, made by Photofrin Medica Inc.) was used. These compounds were employed by dissolving them in a phosphate buffer solution (pH 7.4).

PREPARATION EXAMPLE 1

Preparation of Mono-L-Aspartyl Chlorin $e_6$

Chlorin $e_6$ was prepared according to the procedure described in Fischer and Stern, Di Chemie Des Pyrroles, Vol. II, second half, Leipzig 1940, Akademische Verlagsgesellschaft, pp. 91–93.

150 mg of chlorine$_6$ (free acid form) and 250 mg of L-aspartic acid di-tert-butyl ester hydrochloride were dissolved in 20 ml of dimethyl formamide. There was made a total of 3–100 mg additions of N,N'-dicyclohexylcarbodiimide at one hour intervals. After 4 hours, the reaction mixture was diluted with 300 ml ether, washed twice with 200 ml H$_2$O, then extracted with 40 ml 1M KOH. The KOH solution was allowed to hydrolyze overnight, then heated to 70° C. for 10 minutes.

The pH of the solution was adjusted to 7, then any residual ether was removed by flash evaporation. The solution was then applied to a reverse phase (C-18 silica) column (1.5 cm φ×30 cm). The product was purified by a stepwise elution of methanol/0.01M $KPO_4$ buffer (pH 6.85). Eluted with 5% methanol until unwanted polar pigments were removed. Monoaspartyl chlorin $e_6$ was eluted off with 6–8% methanol, and unreacted chlorin $e_6$ was removed with 25% methanol.

The product was precipitated at pH 3 after flash evaporating briefly to remove methanol, then washed by the centrifuge 3 times with dilute acetic acid.

The product was dried under vacuum. Yield of mono-L-aspartyl chlorin $e_6$ was 50 mg.

PREPARATION EXAMPLE 2

Preparation of Mono-L-Serinyl Chlorin $e_6$

The chlorin $e_6$ prepared in the like manner as in Preparation Example 1 was used. 100 mg of the chlorine $e_6$ and 35 mg of 1-ethyl-3-(3-dimethylaminopropyl)carbodiimide hydrochloride were dissolved in 2 ml of N,N'-dimethyl formamide. After 5 minutes, 125 mg of L-serine benzyl ester hydrochloride was added, stirred vigorously until solution was complete, then allowed to stand at room temperature for 2 hours. At this time, 0.5 ml of glacial acetic acid was added, then 30 ml of methanol and 12 ml of $H_2O$.

The solution was applied to a C-18 reverse phase column. The column was washed with 100 ml of $H_2O$, then 4 ml of 1M $NH_4OH$, then 50 ml of $H_2O$ again. Eluted the product with MeOH/$H_2O$. Fractions eluted from the column with 30% to 80% MeOH contained product as well as carbodiimide-activated chlorin as determined by TLC on C-18 reverse phase plates with a solvent of 70% MeOH/30% buffer (0.1M sodium phosphate pH 6.85) V/V.

These fractions were pooled and enough 3 N NaOH was added to make the solution 0.1N in NaOH. After 1 hour, the hydrolysis was complete as determined by TLC in the above system. Removed the methanol by rotary evaporation and adjusted the pH of the solution to 7.5 with HCl. The chlorin solution was then reapplied to the same reverse phase column, washed with water, and eluted with MeOH/water using a stepwise gradient solution from 10 to 50% methanol. The fractions containing pure mono-L-serinyl chlorin $e_6$ as determined by TLC (Rf slightly greater than the unsubstituted chlorin $e_6$) were pooled, the methanol was removed by rotary evaporation, and the product was dried as the trisodium salt by lyophilization.

Animal Test

Normal Lewis system LEW/Crj rats (supplied by Japan Charles River) which took artificial rheumatoid arthritis were used for experiments as A. A. rats. These rats are suitable for the tests of this kind because they correspond well to the diseases of mankind.

Adjuvant (0.6 mg/animal) of Mycobacterium tuberculosis H37 RA, made by Difco, was applied to the foot pads of right hind legs of male Lewis system LEW/Crj rats of 8 weeks of age. After the inoculation, the reddening and swelling of legs occurred within 24 hours. After 2 to 3 weeks, chronic proliferative periostitis occurred around joints to exhibit the chronic arthritis.

In the experiments, five rats were used for each group of diagnostic test or therapeutic test with each treating agent, respectively.

Test Apparatus

The apparatus for these experiments included a catheter of 2.1 mm in diameter (made by Sumitomo Electric Industries, Ltd.), an argon dye laser (made by Spectrum Physics) for exciting photosensitive substance and a fluorescence spectrum analyzer system. The wavelengths of the argon dye laser for exciting photosensitive substance could be adjusted to 405 nm, 630 nm or 664 nm corresponding to the absorption bands of the respective substances and it was used at an irradiation dose of 100 mW/cm$^2$. This laser beam was introduced into a quartz fiber bundle of 300 μm in core diameter and it was then passed through the catheter.

Example of Diagnosis 1

After 1, 2, 3 and 4 weeks from the inoculation of adjuvant, A. A. rats were administered with a test compound in an amount of 1 mg per 1 kg body weight through a vein of the tail. Six hours after the administration, the knee joint of right hind leg which was inoculated with the adjuvant was cut open under the anesthesia with Nembutal and a laser beam of 405 nm was applied to the lesion using a endoscopic catheter through which the laser beam was passed. The specific fluorescence spectrum generated by the substance taken in the affected lesion (hyperplastic synovial membrane) was observed by a fluorescence analyzer. The intensity of fluorescence was calculated from the integrated area on fluorescence spectrum in the range of 600–700 nm and the obtained values were adopted as criteria for accumulated compounds.

After the photodynamic diagnosis, the animals were sacrificed under anesthesia, the knee joints were resected and served for the specimens. The specimens were subjected to histologic inspection with hematoxylin-eosin stain to compare the intensity of fluorescence and the degree of inflammation.

Normal rats of the same weeks of age were used as basic controls. As comparative examples, the A. A. rats in similar conditions of disease were administered with Photofrin II and they were subjected to similar tests.

Example of Therapeutic Treatment 1

According to the therapeutic conditions indicated in Table 3, three weeks after the inoculation of adjuvant, A. A. rats were administered with test compounds in an amount of 0.5 mg per 1 kg body weight through a vein in the tail. Six hours after the administration, the knee joint of right hind leg which was inoculated with the adjuvant was cut open under the anesthesia with Nembutal and a laser beam was applied directly to the joint cavity. The specific fluorescence spectrum generated by the substance taken in the affected lesion (hyperplastic synovial membrane) was observed by a fluorescence analyzer. The therapeutic treatment was then carried out by applying 50 J/cm$^2$ of 405 nm to 664 nm laser beam to the affected lesion in which it was observed that sufficient quantity of the compound was taken. After the treatment, the incision was sutured and an antibiotic was injected in the wound and joint cavity and the rats were bred for 1 week. One week after the treatment, 1 mg/kg of the same test compounds were administered and photodynamic diagnosis was done. After the diagnosis, the animals were sacrificed under anesthesia and the knee joints were resected and served for the specimens. The specimens were subjected to histologic inspection with hematoxylin-eosin stain to compare the intensity of fluorescence and the degree of inflammation.

The A. A. rats in similar conditions of disease were applied with 50 J/cm$^2$ without administering the test compound were used as controls. As comparative examples, the A. A. rats in similar conditions of disease were administered with Photofrin II and they were subjected to similar tests.

TABLE 3

Method of Therapeutic Treatment

| Compound | Dose mg/kg | Time(*) hrs | Laser Wavelength nm | Laser Intensity mW/cm$^2$ | Irradiation J/cm$^2$ |
|---|---|---|---|---|---|
| Photofrin II | 0.5 | 6 | 405 | 100 | 50 |
| Photofrin II | 0.5 | 6 | 630 | 100 | 50 |
| NPe$_6$ | 0.5 | 6 | 405 | 100 | 50 |
| NPe$_6$ | 0.5 | 6 | 664 | 100 | 50 |
| Control | — | — | 664 | 100 | 50 |

(*)Time length from dosage to irradiation

Test Result 1

The results of Diagnosis 1 are described in the following.

Each compound was administered to A. A. rats of 3 weeks after the inoculation of adjuvant, which rats suffered from adjuvant arthritis. A laser beam was applied to knee joint and the intensity of fluorescence of the compound in the knee joint was determined by photodynamic diagnosis The results are shown in Table 4.

As a result, the intensity of fluorescence in the group of Photofrin II in the arthritic lesion (hyperplastic synovial membrane) was 3.5, meanwhile the value was 1.2 in other cartilage of normal tissue. In Achilles tendon and muscle of normal tissue, the values were 0.5. On the other hand, the intensity of fluorescence in the group of NPe$_6$ in the arthritic lesion (hyperplastic synovial membrane) was 16.0, meanwhile the value was 1.0 in other cartilage of normal tissue. In Achilles tendon and muscle of normal tissue, the values were 0.2.

In the normal rats of the same week of age, the intensity of fluorescence of Photofrin II group in the normal synovial membrane was 0.2, and the fluorescence was not detected in other normal tissues of cartilage, Achilles tendon and muscle. Also, the intensity of fluorescence of NPe$_6$ group in the normal synovial membrane was 0.2, and the fluorescence was not detected in other normal tissues of cartilage, Achilles tendon and muscle.

TABLE 4

Fluorescence Intensities in Photodynamic Diagnosis in Various Tissues Including Affected Lesion (Hyperplastic Synovial Membrane)

| | Medical Agent | |
|---|---|---|
| Tissue | Photofrin II | NPe$_6$ |
| Adjuvant Arthritis Rats | | |
| Affected Lesion (Hyperplastic Synovial membrane) | 3.5 | 16.0 |
| Cartilage | 1.2 | 1.0 |

TABLE 4-continued

Fluorescence Intensities in Photodynamic Diagnosis in Various Tissues Including Affected Lesion (Hyperplastic Synovial Membrane)

| | Medical Agent | |
|---|---|---|
| Tissue | Photofrin II | NPe$_6$ |
| Achilles tendon | 0.5 | 0.2 |
| Muscle | 0.5 | 0.2 |
| Normal Rats | | |
| Affected Lesion | 0.2 | 0.2 |
| Cartilage | 0.0 | 0.0 |
| Achilles tendon | 0.0 | 0.0 |
| Muscle | 0.0 | 0.0 |

Similar diagnosis was carried out by administering NPe$_6$ to A. A. rats which were different in the degree of inflammation with the passage of 1 to 4 weeks after the inoculation of adjuvant. By measuring intensities of fluorescence, the correlation between the measured intensities and the degree of inflammation in the histological diagnosis was investigated. The results are shown in Table 5.

The fluorescence intensity of synovial cells of 1 week after the adjuvant inoculation was 2.0. Almost no fluorescence was observed in other normal tissues of cartilage, Achilles tendon and muscle. According to the histological diagnosis on the same lesions, the growth of synovial cells was not so large and the cartilage was normal (+1). The swelling of right leg which was inoculated with adjuvant was slight.

The fluorescence intensity of synovial cells of 2 weeks after the adjuvant inoculation was 10.5. Almost no fluorescence was observed in other normal tissues of cartilage, Achilles tendon and muscle. According to the histological diagnosis on the same lesions, the growth of synovial cells was observed (+4) and the degree of swelling was more than 2 times the normal value.

The fluorescence intensities of synovial cells of 3 and 4 weeks after the adjuvant inoculation were 16.0 in both cases. In other normal tissues, the values were 1.0 in cartilage and 0.2 in Achilles tendon and muscle. According to the histological diagnosis on the same lesions, the growth of synovial cells was intense and the buildup of villi and the formation of pannus due to granulation (+5) were observed. The swelling was more than 2 times the normal value. The above observation indicates the arthritis due to the adjuvant arthritis.

As described above, the fluorescence intensity of NPe$_6$ has a correlation to the degree of adjuvant arthritis. Accordingly, the degree of inflammation can be determined by comparing the intake of NPe$_6$.

TABLE 5

Fluorescence Intensity of NPe$_6$ vs. Degree of Rheumatoid Arthritis and Results of Diagnosis

| | Weeks of Age of A. A. Rats after Inoculation of Adjuvant | | | | |
|---|---|---|---|---|---|
| Test Item | 0 week (Normal) | 1 week | 2 weeks | 3 weeks | 4 weeks |
| Intensity of Fluorescence | | | | | |
| Cartilage | 0.0 | 0.0 | 0.2 | 1.0 | 1.0 |
| Achilles tendon | 0.0 | 0.0 | 0.0 | 0.2 | 0.2 |

TABLE 5-continued

Fluorescence Intensity of $NPe_6$ vs. Degree of Rheumatoid Arthritis and Results of Diagnosis

| Muscle | 0.0 | 0.0 | 0.0 | 0.2 | 0.2 |
|---|---|---|---|---|---|
| Synovial Membrane | 0.0 | 2.0 | 10.5 | 16.0 | 16.0 |
| Results of Diagnosis | | | | | |
| Histological[1] Diagnosis | ±0 | +1 | +4 | +5 | +5 |
| Degree of[2] Swelling | 5.5 | 7.5 | 12.5 | 13.0 | 13.0 |

Notes:
[1]Histological Diagnosis:
The degree of the growth of synovial cells in the affected lesion and the formation of pannus.
Evaluation:
±0: Indicates the state of normal form and quantity of synovial cells and normal cartilage.
↓
+5: Indicates the state of hyperplastic synovial cells and formation of pannus.
[2]Degree of Swelling:
The diameter (mm) of a right leg which was inoculated with adjuvant.

Test Result 2

The results of Therapeutic Treatment 1 are described in the following.

Each compound was administered to A. A. rats of 3 weeks after the inoculation of adjuvant, which rats suffered from rheumatoid arthritis. Photodynamic diagnosis was carried out by applying a laser beam to a knee joint cavity so as to confirm the sufficient intake of the medical agent. The therapeutic treatment was done by irradiating the affected lesion (hyperplastic synovial membrane) with 50 J/cm² of laser beam. One week after the treatment, the same medical agent was administered for photodynamic diagnosis, thereby comparing the obtained value with the value before the therapeutic treatment. The results are shown in the following Table 6.

As a result, the intensities of fluorescence in Photofrin II group in the affected lesion were 3.5 to 3.6 before the therapeutic treatment and 1.8 to 2.0 after the treatment. Meanwhile, the intensities of fluorescence in $NPe_6$ group in the affected lesion were 16.0 to 16.2 before the treatment and 1.9 to 2.4 after the treatment.

In the A. A. rats with the same disease without the dose of medical agent, fluorescence was not observed in both before and after the therapeutic treatment.

In the group of Photofrin II, the average ratio of fluorescence intensities after the therapeutic treatment to those before the treatment in the affected lesions was 54%. Meanwhile, in the group of $NPe_6$, the average ratio was as low as 13%. Accordingly, it was ascertained that the degree of inflammation could be alleviated more effectively in the group of $NPe_6$ by the therapeutic treatment as compared with 14 the cases in the group of Photofrin II.

TABLE 6

Fluorescence Intensities of Medical Agents before and after Photodynamic Therapy in Affected Lesion (Hyperplastic Synovial Membrane)

| | Item | | |
|---|---|---|---|
| | Wave[1] | Fluorescence Intensity[2] | |
| Medical Agent | Length (nm) | Before Treatment | After Treatment |
| Photofrin II | 405 | 3.5 | 2.0 |
| Photofrin II | 630 | 3.6 | 1.8 |
| $NPe_6$ | 405 | 16.0 | 2.4 |
| $NPe_6$ | 664 | 16.2 | 1.9 |
| No Dosage | 664 | 0.0 | 0.0 |

Notes:
[1]Wavelength: The wavelength of applied laser beam used for the therapeutic treatment.
[2]Fluorescence Intensity:
The intensities of fluorescence which was observed by photodynamic diagnosis in treated lesions at the times before the treatment and 1 week after the treatment.

Shown in Table 7 are the comparative results of histological diagnosis and ocular diagnosis with preparing tissue specimens of treated lesions. In the therapy group of Photofrin II, slight changes in synovial cells were observed without any significant difference and marked therapeutic effect was not obtained (+3).

On the other hand, in the therapy group of $NPe_6$, synovial cells were subjected to vacuolation or atrophy and the exfoliation of synovial cells was observed. Owing to the above effect, the swelling was relieved and the improvement in the affected lesion was observed (±0 to +1 ).

In the group of $NPe_6$ applying laser beams of two kinds of 405 nm and 664 nm in wavelength gave similar high therapeutic effects.

In the group of no dosage for the A. A. rats of similar condition of disease, no change of affected lesion was observed by the irradiation with 50 J/cm² laser beam (+5).

As described above, the therapeutic effect in the group of $NPe_6$ was high as compared with the effect in the group of Photofrin II and the alleviation and improvement of rheumatoid arthritis were apparently observed.

TABLE 7

Results of Photodynamic Therapy

| Medical Agent | Wavelength[1] (nm) | Intensity of[2] Fluorescence | Histological[3] Diagnosis | Ocular[4] Diagnosis |
|---|---|---|---|---|
| Photofrin II | 405 | 2.0 | +3 | +3 |
| Photofrin II | 630 | 1.8 | +3 | +3 |
| $NPe_6$ | 405 | 2.4 | +1 | +1 |
| $NPe_6$ | 664 | 1.9 | ±0 | ±0 |
| No Dosage | 664 | 0.0 | +5 | +5 |

Notes:
[1]Wavelength:
The wavelength of laser beam for the irradiation of therapeutic treatment.
[2]Intensity of Fluorescence:
The intensity of fluorescence in the treated lesion which was observed by photodynamic diagnosis carried out 1 week after the therapeutic treatment.
[3]Histological Diagnosis:
The degree of the hyperplasia of synovial cells in the affected TABLE 7-continued Results of Photodynamic Therapy lesion and the formation of pannus.
Evaluation:
±0: Indicates the state of normal form and quantity of synovial cells and normal cartilage.
↓
+5: Indicates the state of hyperplastic synovial cells and formation of pannus.
(4) Ocular Diagnosis (Degree of swelling):
Indicates the degree of swelling and changes observed by visual observation.
Evaluation:
±0: Indicates that the diameter of right leg is in normal value.
↓
+5: Indicates the swollen right leg and accompanying functional disorder.

Concerning the above compounds, the test of acute toxicity among toxicological properties was carried out.

$NPe_6$ was intravenously administered to rats (strain: Sprague-Dawley) to determine the 50% lethal dose ($LD_{50}$). The value of $LD_{50}$ in male was 176 mg/kg and 184 mg/kg in female. The $LD_{50}$ values in the intravenous administration to mice (strain: C3H/HEJ) were 214 mg/kg in male and 187 mg/kg in female.

SUMMARY OF TEST RESULTS (1) The photodynamic therapy using $NPe_6$ was found to be effective for the regression of rheumatoid arthritis and for the curing of lesion. In comparison with the treatment using the known Photofrin II, a higher therapeutic effect (regression of arthritic lesion) can be expected when the same quantities of treating agents are administered to the arthritic lesion on the same degree of disease.

(2) In the photodynamic diagnosis with $NPe_6$, more excellent selective intake in comparison with Photofrin II in the arthritic lesion was confirmed. Even when a small dose of the compound was used, it could identify the arthritic lesion, thereby enabling to concentrate the treatment effect specifically to the arthritic lesion.

(3) The fluorescence intensity of $NPe_6$ was correlative to the degree of seriousness of rheumatoid arthritis. Accordingly, the degree of disease can be determined by comparing the intake amount of $NPe_6$.

(4) In the use of $NPe_6$, the treatment with laser beams of either 405 nm or 664 nm in wavelength corresponding to its absorption bands, can provide high therapeutic effects.

EFFECT OF THE INVENTION

The above-described compound was administered to mammals which were suffered from arthritis and photodynamic diagnosis and photodynamic therapy were carried out. As a result, the following effects were ascertained.

(1) The disease can be diagnosed and treated directly and exactly because the medical compound is selectively accumulated in the arthritic lesion.

(2) One week after the therapeutic treatment, synovial membrane in abnormal growth in a joint is subjected to vacuolation or atrophy and the swelling is relieved.

(3) In comparison with the conventionally used Photofrin II or the like, more distinct therapeutic effect can be expected when the same quantities of medical agents are used for arthritic lesions of the same degree in seriousness.

What is claimed is:

1. A method for the diagnosis of arthritis of mammals, which comprises administering to a mammal an effective amount of a fluorescent tetrapyrrole compound that accumulates in an arthritic lesion within said mammal and applying light of sufficient wavelength and intensity to produce fluorescence in said arthritic lesion, wherein said tetrapyrrole compound is selected from the group consisting of tetrapyrrole carboxylic acids having at least one carboxyl group represented by the following general formula, and corresponding dihydrotetrapyrrole or tetrahydrotetrapyrrole carboxylic acids, and monoamides, diamides and polyamides of said tetrapyrrole carboxylic acids with aminomonocarboxylic acids or dicarboxylic acids, and their pharmacologically acceptable salts:

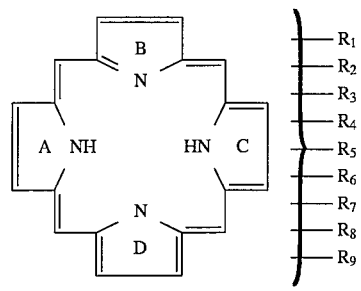

wherein, $R_1$ is methyl $$\begin{bmatrix} -H \\ -CH_3 \end{bmatrix} \text{ or } \begin{bmatrix} -OH \\ -CH_3 \end{bmatrix};$$

$R_2$ is H, vinyl, ethyl, —CH(OH)CH$_3$, acetyl,

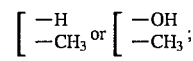

—CH$_2$CH$_2$COOH or =CHCHO;

$R_3$ is methyl, $$\begin{bmatrix} -H \\ -CH_3 \end{bmatrix} \text{ or } \begin{bmatrix} -CH_3 \\ -OH \end{bmatrix};$$

$R_4$ is H, vinyl, ethyl, —CH(OH)CH$_3$, —CH$_2$CH$_2$COOH, =CHCHO or

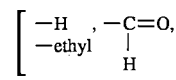

$R_5$ is methyl;

$R_6$ is H, —CH$_2$CH$_2$COOH, —CH$_2$CH$_2$COOR or —COOH;

$R_7$ is —CH$_2$CH$_2$COOH, —CH$_2$CH$_2$COOR or

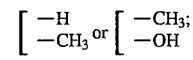

$R_8$ is methyl or

$R_9$ is H, —COOH, —CH$_2$COOH or methyl; provided that when $R_1$, $R_2$, $R_3$, $R_4$, $R_7$ and $R_8$ represent two substituents or are divalent and attached to the same carbon, the respective pyrrole ring to which attached is a dihydropyrrole;

R is lower alkyl or benzyl;

$R_6$ and $R_9$, taken together are

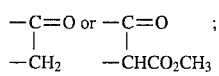

with the proviso that at least one of $R_1$ to $R_9$ is a free carboxyl group.

2. The method as claimed in claim 1, wherein the lesion to be diagnosed by said method is a hyperplastic granulation of synovial membrane in a joint.

3. The method as claimed in claim 1, wherein the wavelength of said light is about 300 nm to about 800 nm.

4. The method as claimed in claim 3, wherein said wavelength is about 360 nm to about 760 nm.

5. The method as claimed in claim 1, wherein the intensity of said light is about 10 mW/cm² to about 1000 mW/cm².

6. The method as claimed in claim 1, wherein the dose of said tetrapyrrole compound is about 0.1 to 20 mg/kg.

7. The method as claimed in claim 1, wherein said amino-monomonocarboxylic acids or dicarboxylic acids are natural α-amino-monocarboxylic acids or α-amino-dicarboxylic acids.

8. The method as claimed in claim 1, wherein said tetrapyrrole carboxylic acid has at least 3 carboxyl groups.

9. The method as claimed in claim 8, wherein said tetrapyrrole carboxylic acid is represented by the following general formula:

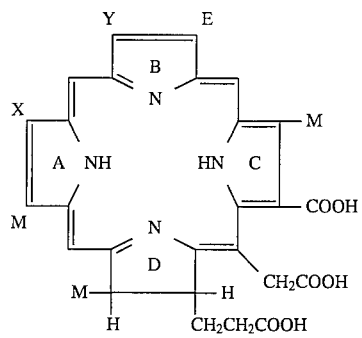

wherein, X is H, vinyl, ethyl, acetyl or formyl; Y is methyl or formyl; M is methyl; and E is ethyl.

* * * * *

UNITED STATES PATENT AND TRADEMARK OFFICE
CERTIFICATE OF CORRECTION

PATENT NO. : 5,567,409
DATED : October 22, 1996
INVENTOR(S) : Katsuo Aizawa, et al.

It is certified that error appears in the above-indentified patent and that said Letters Patent is hereby corrected as shown below:

Column 5, line 50, Table 2: "$e^6$" should read -- $e_6$ --

Column 7, line 45: "$\epsilon$-Alanyl" should read -- $\beta$-Alanyl --

Columns 7-15: all instances of "chlorine$_4$" should read --chlorin $e_4$--

Columns 7-15: all instances of "chlorine$_6$" should read --chlorin $e_6$--

Column 10, line 50: "Di-Olycyl" should read --Di-glycyl--

Column 12, line 24: after "coproporphyrin" insert --III--

Column 14, line 55: "Olutaminyl" should read --glutaminyl--

Column 15, line 40: "di-L-a" should read --di-L-$\alpha$ --

Column 15, line 65: "chlorine $e_6$" should read --chlorin $e_6$--

UNITED STATES PATENT AND TRADEMARK OFFICE
CERTIFICATE OF CORRECTION

PATENT NO. : 5,567,409
DATED : October 22, 1996
INVENTOR(S) : Katsuo Aizawa, et al.

It is certified that error appears in the above-indentified patent and that said Letters Patent is hereby corrected as shown below:

Column 17, line 15: "FOr" should read --For--

Column 18, line 45: "Npe6" should read --Npe$_6$--

Column 21, line 30: after "diagnosis" insert --.--

Signed and Sealed this

Tenth Day of March, 1998

BRUCE LEHMAN

*Attest:*

*Attesting Officer*  *Commissioner of Patents and Trademarks*